(12) United States Patent
Okamoto et al.

(10) Patent No.: US 9,090,869 B2
(45) Date of Patent: *Jul. 28, 2015

(54) TEMPERATURE RESPONSIVE SHEET THAT DISPLAYS REVERSIBLE PROPERTIES AND CELL SHEET PRODUCTION METHOD USING SAME

(75) Inventors: Kouji Okamoto, Iizuka (JP); Erika Yoshino, Kitakyushu (JP)

(73) Assignee: KYUSHU INSTITUTE OF TECHNOLOGY, Kitakyushu-Shi (JP)

( * ) Notice: Subject to any disclaimer, the term of this patent is extended or adjusted under 35 U.S.C. 154(b) by 102 days.

This patent is subject to a terminal disclaimer.

(21) Appl. No.: 13/703,318

(22) PCT Filed: Jun. 9, 2011

(86) PCT No.: PCT/JP2011/063265
§ 371 (c)(1),
(2), (4) Date: Feb. 8, 2013

(87) PCT Pub. No.: WO2011/155565
PCT Pub. Date: Dec. 15, 2011

(65) Prior Publication Data
US 2013/0130384 A1 May 23, 2013

(30) Foreign Application Priority Data
Jun. 10, 2010 (JP) .................. 2010-132976

(51) Int. Cl.
*C12M 1/00* (2006.01)
*C12N 5/00* (2006.01)
*A61L 27/22* (2006.01)
*C07K 14/78* (2006.01)
*C12M 1/12* (2006.01)

(52) U.S. Cl.
CPC ............ *C12N 5/0068* (2013.01); *A61L 27/227* (2013.01); *C07K 14/78* (2013.01); *C12M 25/14* (2013.01); *C12N 2533/50* (2013.01); *C12N 2539/10* (2013.01)

(58) Field of Classification Search
USPC .......................................... 435/397; 530/353
See application file for complete search history.

(56) References Cited

U.S. PATENT DOCUMENTS

| 2004/0028657 A1 | 2/2004 | Okano et al. |
| 2008/0096812 A1 | 4/2008 | Okamoto et al. |
| 2008/0118474 A1 | 5/2008 | Okano et al. |

FOREIGN PATENT DOCUMENTS

| WO | WO 02/10349 A1 | 2/2002 |
| WO | WO 2005/103233 A1 | 11/2005 |
| WO | WO 2006/046626 A1 | 5/2006 |

OTHER PUBLICATIONS

International Seacrch Report, dated Jul. 5, 2011, issued in PCT/JP2011/063265.
Maegawa et al., "Characteristics of self-assemby of the chemically-modified soluble elastic and type I collagen in the coexisted state", Kitakyushu Iko Gakujutsusha Kyokaishi, vol. 20, pp. 25-28, 2010.
Mie, M. et al., "Novel Extracellular Matrix for Cell Sheet Recovery Using Genetically Engineered Elastin-Like Protein", Journal of Biomedical Materials Research. Part B: Applied Biomaterials, vol. 86, No. 1, pp. 283-290, 2007.
Mizushima et al., "Kokino Saibo Sheet Kochiku no Tameno Jinko Tanpakushitsu Zairyo no Kaihatsu", The Chemical Society of Japan Dai 86 Shunki Nenkai Koen Yokoshu II, p. 899, 4G4-11, 2006.

*Primary Examiner* — Sharmila G. Landau
*Assistant Examiner* — Damon B Bowe
(74) *Attorney, Agent, or Firm* — Birch, Stewart, Kolasch & Birch, LLP

(57) ABSTRACT

A temperature responsive sheet is disclosed that comprises a chemically modified water-soluble elastin obtained by N-acylating at least some of the primary amines and secondary amines contained in a high molecular weight water-soluble elastin molecule and coupling some or all of carboxyl groups contained in the molecule with a glycine alkyl ester. Also is disclosed a process for producing a cell sheet that comprises preparing above the temperature responsive sheet a film that functions as a scaffold for animal cells, culturing specific cells on the film so as to prepare a cell sheet, and subsequently separating the cell sheet and the temperature responsive sheet comprising the chemically modified water-soluble elastin under conditions of no greater than the culturing temperature for the cells.

9 Claims, 8 Drawing Sheets

SEQUENCE LISTING

```
<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: the repetive sequence that is present in an
      elastin

<400> SEQUENCE: 1

Val Pro Gly Val Gly
1               5

<210> SEQ ID NO 2
<211> LENGTH: 4
<212> TYPE: PRT
<213> ORGANISM: Artificial Sequence
<220> FEATURE:
<223> OTHER INFORMATION: the repetive sequence that is present in an
      elastin

<400> SEQUENCE: 2

Val Pro Gly Gly
1

<210> SEQ ID NO 3
```

```
<211> LENGTH: 5
<212> TYPE: PRT
<213> ORGANISM: Artificial Sequence
<220> FEATURE:
<223> OTHER INFORMATION: the repeptive sequence of elastin-derived
      polypeptides

<400> SEQUENCE: 3

Pro Gly Val Gly Val
1               5

<210> SEQ ID NO 4
<211> LENGTH: 5
<212> TYPE: PRT
<213> ORGANISM: Artificial Sequence
<220> FEATURE:
<223> OTHER INFORMATION: the repeptive sequence of elastin-derived
      polypeptide

<400> SEQUENCE: 4

Gly Val Gly Val Pro
1               5

<210> SEQ ID NO 5
<211> LENGTH: 5
<212> TYPE: PRT
<213> ORGANISM: Artificial Sequence
<220> FEATURE:
<223> OTHER INFORMATION: the repeptive sequence of elastin-derived
      polypeptide

<400> SEQUENCE: 5

Val Gly Val Pro Gly
1               5

<210> SEQ ID NO 6
<211> LENGTH: 5
<212> TYPE: PRT
<213> ORGANISM: Artificial Sequence
<220> FEATURE:
<223> OTHER INFORMATION: the repeptive sequence of elastin-derived
      polypeptide

<400> SEQUENCE: 6

Gly Val Pro Gly Val
1               5

<210> SEQ ID NO 7
<211> LENGTH: 4
<212> TYPE: PRT
<213> ORGANISM: Artificial Sequence
<220> FEATURE:
<223> OTHER INFORMATION: the repeptive sequence of elastin-derived
      polypeptide

<400> SEQUENCE: 7

Pro Gly Gly Val
1

<210> SEQ ID NO 8
<211> LENGTH: 4
<212> TYPE: PRT
<213> ORGANISM: Artificial Sequence
<220> FEATURE:
<223> OTHER INFORMATION: the repeptive sequence of elastin-derived
      polypeptide

<400> SEQUENCE: 8
```

```
Gly Gly Val Pro
1

<210> SEQ ID NO 9
<211> LENGTH: 4
<212> TYPE: PRT
<213> ORGANISM: Artificial Sequence
<220> FEATURE:
<223> OTHER INFORMATION: the repetive sequence of elastin-derived
      polypeptide

<400> SEQUENCE: 9

Gly Val Pro Gly
1
```

TEMPERATURE RESPONSIVE SHEET THAT DISPLAYS REVERSIBLE PROPERTIES AND CELL SHEET PRODUCTION METHOD USING SAME

TECHNICAL FIELD

The present invention relates to a temperature responsive sheet exhibiting reversible properties and a process for producing a cell sheet containing cultured cells by use of same.

BACKGROUND ART

In recent years, regenerative medicine employing cell sheet engineering techniques has been attracting attention, and a large number of attempts to graft various types of cell sheets have been carried out. When grafting, a cell sheet is used in methods in which a single layer sheet is grafted, a uniform tissue formed by layering identical cell sheets is grafted, a tissue having a layered structure formed by layering several different types of cell sheets is grafted, etc. 20 to 30 types of cell sheets are currently produced, and progress has been made in clinical applications employing epithelial cell systems such as those of the cornea, retina, skin, the bladder epithelium, and the periodontal ligament.

However, there is a problem with the production of a cell sheet. The problem is that when peeling off cultured cells or a cell sheet from a culture dish, since cells adhere strongly to an adhesion protein on the culture dish, it is necessary to use a proteolytic enzyme, and as a result cells and extracellular matrix are damaged. Recently, a method that does not use a proteolytic enzyme, that is, a method for recovering a cell sheet in which a culture dish surface is coated with an N-isopropylacrylamide polymer (PIPAAm), which is a polyacrylamide for which the surface properties change depending on the temperature, has been developed. PIPAAm is a material whose affinity for water changes greatly on either side of 32° C. When this PIPAAm is fixed to a culture dish surface at a uniform nano-order thickness, the surface becomes hydrophobic at 37° C., which is suitable for culturing cells, and the cells adhere and proliferate. On the other hand, when the temperature is decreased to 32° C. or below after culturing, the surface becomes hydrophilic, and sheet-form cells can be peeled off without being damaged (ref. e.g. Patent Documents 1 and 2).

However, although an acrylamide polymer like PIPAAm does not itself have toxicity such as that shown by an acrylamide monomer, there is a possibility that, in the production process for an acrylamide polymer, unpolymerized acrylamide monomer, which has toxicity, will remain within the polymer, and this problem has been pointed out.

RELATED ART DOCUMENTS

Patent Documents

Patent Document 1: International Patent Application WO 2002-10349
Patent Document 2: International Patent Application WO 2005-103233

SUMMARY OF THE INVENTION

Problems to be Solved by the Invention

It is an object of the present invention to provide a method for recovering sheet-form cultured cells unchanged by producing a temperature responsive sheet that is biologically derived, has very low toxicity, and shows reversible properties, and utilizing these properties.

Means for Solving the Problems

The present inventors have focused attention on a water-soluble elastin, which is a biologically derived material having very low toxicity, as a replacement for PIPAAm and, by utilizing the coacervate-forming ability of a water-soluble elastin, have made an attempt to produce a reversible temperature responsive sheet comprising a chemically modified water-soluble elastin having high molecular aggregation ability by reducing the charge of the water-soluble elastin, and to utilize the sheet for production of a cell sheet. Furthermore, an attempt has been made to produce a polypeptide that has a peptide sequence that is present in an elastin having very low toxicity, showing coacervation, and having high molecular aggregation ability, in order to use it in a reversible temperature responsive sheet.

The present inventors have found that the object can be achieved specifically by modes of the present invention described below.

One mode of the present invention is a temperature responsive sheet comprising a chemically modified water-soluble elastin obtained by N-acylating at least some of the primary amines and secondary amines contained in a water-soluble elastin molecule and coupling at least some of the carboxyl groups contained in the molecule with an amino acid alkyl ester.

Preferred embodiments of the temperature responsive sheet of the present invention are listed below.

The temperature responsive sheet is preferably obtained by N-acetylating at least some of the primary amines and secondary amines and coupling at least some of the carboxyl groups with glycine methyl ester.

The N-acetylation is preferably carried out so that the degree of modification as defined by equation (1) is at least 80 mole %.

$$\text{Degree of modification (mole \%)} = (1-B/A) \times 100 \quad (1)$$

Here, A denotes a value obtained by subtracting the average value of the absorbance (wavelength 345 nm) of a blank from the average value of the absorbance of the water-soluble elastin, and B denotes a value obtained by subtracting the average value of the absorbance (wavelength 345 nm) of a blank from the average value of the absorbance of the N-acetylated water-soluble elastin.

With regard to carboxyl group protection, it is preferable that at least 90 mole % of the carboxyl groups are protected by glycine methyl ester.

With regard to the temperature responsive sheet of the present invention, the chemically modified water-soluble elastin has the property of forming a coacervate at a pH of 7.4 and a temperature of 37° C. and the coacervate dissolving when the temperature is decreased to 20° C. or below, preferably 1° C. to 20° C., and more preferably 1° C. to 15° C.

Furthermore, it is preferable that the water-soluble elastin is a high molecular weight water-soluble elastin obtained by removing a low molecular weight fraction by dialysis.

The temperature responsive sheet of the present invention is preferably used for the preparation of a cell sheet.

A combination of the preferred embodiments is even more preferable.

Another mode of the present invention is a process for producing a cell sheet, comprising a step of preparing a cell sheet above a temperature responsive sheet comprising the chemically modified water-soluble elastin by culturing specific cells, and a step of subsequently separating the temperature responsive sheet and the cell sheet under conditions of no greater than the culturing temperature for the cells.

The production process preferably comprises, subsequent to the step of forming a temperature responsive sheet, a step of forming above the temperature responsive sheet a gel film that functions as a scaffold for cells. The film functioning as a scaffold is preferably a gel film selected from the group consisting of so-called extracellular matrices. Specifically, the film functioning as a scaffold is preferably a gel film selected from the group consisting of collagen, fibronectin, laminin, polylysine, and gelatin, more preferably a gel film selected from the group consisting of collagen, polylysine, and gelatin, and particularly preferably a gel film of collagen.

The 'gel film that functions as a scaffold for cells' may comprise as a main component an extracellular matrix such as collagen and, in addition, as an optional component, a small amount of a different type of extracellular matrix that promotes cell adhesion/cell proliferation, such as fibronectin, laminin, vitronectin, tenascin, thrombospondin, entactin, osteopontin, von Willebrand factor, fibrinogen, chondroitin-6 sulfate, dermatan sulfate, keratan sulfate, heparan sulfate, heparin, or hyaluronic acid.

Yet another mode of the present invention is chemical synthesis of a polypeptide having a peptide sequence that is present in the elastin exhibiting coacervation in the same manner as for the chemically modified water-soluble elastin, and use of a sheet comprising the polypeptide as a main component in a reversible temperature responsive sheet. Comprising as a main component means being at least 90 wt %, and it is preferably a sheet comprising the polypeptide alone. This polypeptide is explained in detail later.

Effects of the Invention

In accordance with the present invention, a cell sheet can be produced unchanged and without being damaged by utilizing the reversible temperature responsiveness of the chemically modified water-soluble elastin. A conventional temperature responsive culture dish employing PIPAAm has a possibility of toxic acrylamide monomer remaining, but in the present invention cultured cells can be recovered in the form of a sheet using a biologically derived safe protein or polypeptide simply by decreasing the temperature in the same way.

EXPLANATION OF REFERENCE NUMERALS AND SYMBOLS

1: Collagen gel
2: N-Ac-Ela-O-Gly-OMe coacervate
3: Fibroblasts
4: Cell sheet
5: State in which N-Ac-Ela-O-Gly-OMe coacervate has dissolved and disappeared

MODES FOR CARRYING OUT THE INVENTION

Modes of the present invention are explained below in sequence.

Figure 1:
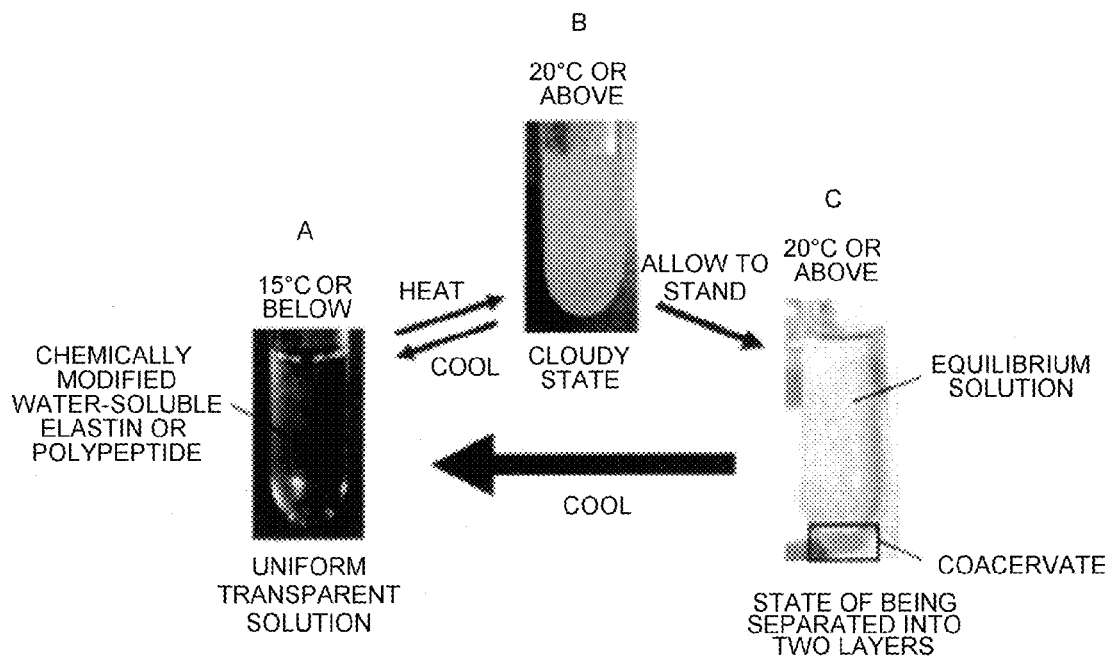
FIG. 1 shows a diagram showing the coacervation of chemically modified water-soluble elastin and polypeptide.
Figure 2:
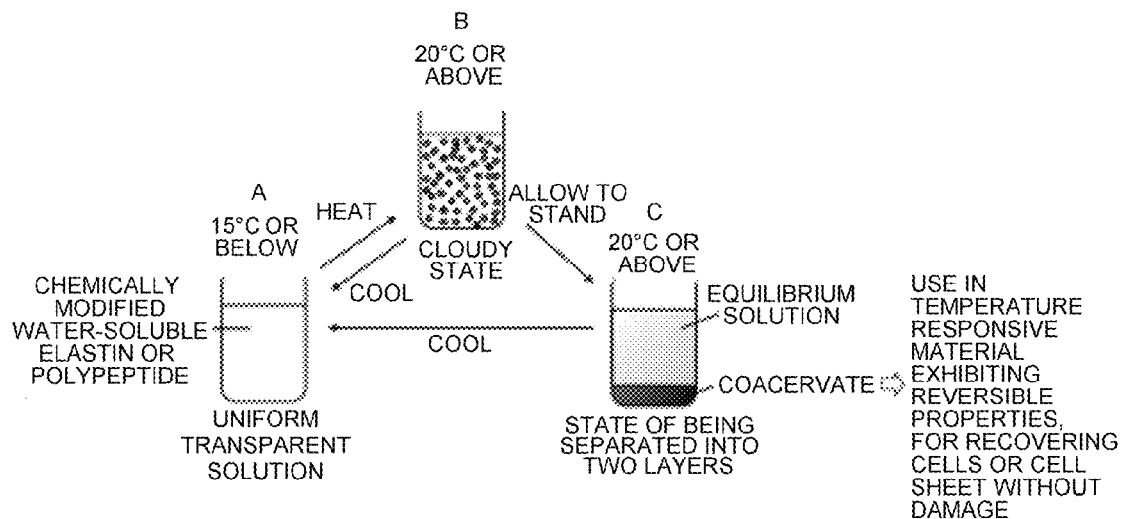
FIG. 2 shows a diagram schematically showing the coacervation of chemically modified water-soluble elastin and polypeptide.

Referring to FIG. 1 and FIG. 2, coacervation of a water-soluble elastin, the chemically modified water-soluble elastin of the present invention that is a derivative thereof (in the present invention, also called a 'chemically modified water-soluble elastin'), and a polypeptide having a peptide sequence that is present in elastin are explained.

FIG. 1 is a diagram showing coacervation of a chemically modified water-soluble elastin and the polypeptide. In FIG. 1, as shown in A, the chemically modified water-soluble elastin and the polypeptide are uniform transparent solutions at 15° C. or below. Similarly, as shown in B, when heated to 20° C. or above, a phase transition occurs and a cloudy state comprising an equilibrium solution and coacervate liquid droplets is attained. This cloudy state returns to the original uniform transparent solution when cooled. As shown in C, when allowed to stand at 20° C. or above as it is, the coacervate liquid droplets unite with each other to become larger liquid droplets and sink as a pale-yellow highly viscous coacervate layer, thereby giving separation into two layers, that is, the equilibrium solution and the coacervate. When this two layer separated state is cooled, the coacervate dissolves, and there is a return to the original uniform transparent solution.

FIG. 2 is a diagram schematically showing coacervation of the chemically modified water-soluble elastin and the polypeptide. In FIG. 2, since the lower coacervate layer in C dissolves when cooled and returns to the original uniform transparent solution, this coacervate may be used as a temperature responsive material for recovering cells or a cell sheet without damaging them.

For example, an aqueous solution of the chemically modified water-soluble elastin or the polypeptide is a uniform transparent solution at low temperature, becomes cloudy when heated, and separates into two layers, that is, a transparent equilibrium solution (upper layer) and a pale-yellow highly viscous coacervate (lower layer) when allowed to stand as it is. This process is reversible and these two layers return to the original uniform solution when cooled. The present invention produces a cell sheet and recovers it without damaging cells and extracellular matrix by utilizing such reversible properties.

The chemically modified water-soluble elastin in the present invention is obtained by N-acylating at least some of the primary amines and secondary amines contained in a water-soluble elastin molecule and coupling at least some of the carboxyl groups contained in the molecule with an amino acid alkyl ester. Examples of the N-acylation include N-formylation, N-acetylation, and N-benzoylation, but N-acetylation is preferable. Furthermore, N-acylation may employ a urethane type or an alkyl type. The amino acid used in coupling is selected from the approximately 20 types that constitute proteins, such as glycine, valine, and phenylalanine.

In the present invention, it is preferable to use a high molecular weight water-soluble elastin, 'high molecular weight' meaning a water-soluble elastin from which relatively low molecular weight (about 5,000 or below) components have been removed. It is preferable to remove low molecular weight components by dialysis using a dialysis membrane having a molecular weight cut-off of 6,000 to 8,000. The molecular weight of the main high molecular weight water-soluble elastin is preferably at least about 10,000, and more preferably about 30,000 to 300,000.

In the present invention, the 'water-soluble elastin' is one obtained by subjecting a water-insoluble elastin to partial hydrolysis, and specifically it is obtained by treating animal body tissue such as animal aorta, nuchal ligament, or fish aortic bulb with an acidic solubilizing liquid or an alkaline solubilizing liquid. Representative examples of the water-soluble elastin include α-elastin and β-elastin, which are obtained by treatment with hot oxalic acid, and κ-elastin, which is obtained by treating elastin with alkaline ethanol. Other examples include an elastin digest obtained by treatment with an enzyme such as elastase, and tropoelastin, which is a precursor in the elastin biosynthetic pathway. The solubility of the water-soluble elastin in water is at least about 0.001 mg/mL but no greater than about 600 mg/mL at 5° C., and is preferably at least 1 mg/mL but no greater than 600 mg/mL.

Prior to partial hydrolysis of the water-insoluble elastin, it is preferable to carry out a treatment for fragmenting elastin-containing body tissue, a treatment with hot water and hot dilute aqueous alkali solution, a delipidation treatment such as extraction with acetone, extraction and removal of unwanted sodium chloride-soluble protein, etc.

When producing the chemically modified water-soluble elastin, the N terminal of a water-soluble elastin and an amino group, etc. of the side chain of an amino acid residue such as lysine or arginine are subjected to N-acylation, and the C terminal and a carboxyl group, etc. of the side chain of an amino acid residue such as aspartic acid or glutamic acid are subsequently coupled with the amino group of an amino acid alkyl ester, thus giving a chemically modified water-soluble elastin. It is surmised that due to the amino group, etc. and the carboxyl group, etc. being modified by chemical modification, the charge of the elastin is decreased or eliminated, as a result hydrophobic interaction between elastin molecules increases, and the chemically modified water-soluble elastin thus obtained has superior self-assembly properties compared with the unmodified elastin.

A process for producing a water-soluble elastin, a method for chemically modifying a water-soluble elastin, a method for preparing a temperature responsive sheet comprising the chemically modified water-soluble elastin of the present invention, and a method for recovering a cell sheet without it being damaged by preparing a cell sheet by culturing specific cells on the temperature responsive sheet obtained, and subsequently separating the temperature responsive sheet and the cell sheet under conditions of no greater than the culturing temperature of the cells are explained in detail below.

With regard to the process for producing a water-soluble elastin, various processes have been proposed. The processes below, which have been proposed by the present inventors (ref. JP-A-2007-45722 (JP-A denotes a Japanese unexamined patent application publication)), are preferable.

The first process produces a water-soluble elastin by obtaining an insoluble elastin by subjecting animal body tissue to a treatment involving the removal of collagen and other unwanted protein, and subsequently immersing and dissolving this insoluble elastin in an acidic solubilizing liquid containing oxalic acid, etc. or an alkaline solubilizing liquid containing sodium hydroxide, etc. The treatment involving the removal of collagen and other unwanted protein is preferably carried out by immersing animal body tissue at 90° C. to 105° C. for 5 to 60 minutes in an alkaline solution containing at least one of sodium hydroxide, potassium hydroxide, calcium hydroxide, and barium hydroxide, the total amount of sodium hydroxide, potassium hydroxide, calcium hydroxide, and barium hydroxide added to this alkaline solution being 0.03 to 0.5 mol per L, and preferably 0.05 to 0.3 mol per L. Furthermore, when removing collagen and other unwanted protein, it is also preferable to carry out, prior to the treatment with an alkaline solution, an immersion treatment (pre-treatment) in which animal body tissue is immersed in a salt solution containing any one of sodium chloride, potassium chloride, calcium chloride, and barium chloride.

The animal body tissue is not particularly limited, but from the viewpoint of the content of elastin being high, it is preferable to use nuchal ligament or aortic blood vessel obtained from a mammal such as a pig, a horse, a cow, or a sheep. The aortic bulb, etc. of fish, which has a high elastin content, may also be used. It is desirable to first homogenize animal body tissue using a homogenizer. The homogenization may be carried out using a device such as a mixer or a meat grinder that can fragment animal body tissue, preferably into a size of no greater than 3 mm square, and more preferably into a paste. The smaller the fragmented particles of animal body tissue, the higher the efficiency of removal of collagen and other unwanted protein, which is preferable. The homogenized animal body tissue may be subjected to a delipidation treatment by for example boiling in hot water or a hot dilute aqueous alkali solution or treating with an organic solvent.

As the solubilizing liquid, an acidic solution containing at least one of oxalic acid, formic acid, acetic acid, succinic acid, malic acid, tartaric acid, citric acid, benzoic acid, betaine, difluoroacetic acid, trifluoroacetic acid, phosphoric acid, sulfamic acid, perchloric acid, and trichloroacetic acid may be used. The total amount of acid in this acidic solution is 0.05 to 5 mol per L, and preferably 0.1 to 2 mol per L, and the liquid temperature is preferably set at 90° C. to 105° C.

The solubilizing liquid may be an alkaline solution containing at least one of sodium hydroxide, potassium hydroxide, calcium hydroxide, and barium hydroxide. The total amount of sodium hydroxide, potassium hydroxide, calcium hydroxide, and barium hydroxide added to this alkaline solution is 0.05 to 5 mol per L, and preferably 0.05 to 2 mol per L, and the liquid temperature of the alkaline solution is preferably set at 90° C. to 105° C.

The second process is a process for producing a water-soluble elastin by carrying out in sequence a pre-treatment step comprising at least one of a treatment of removing an unwanted portion of animal body tissue, a treatment of delipidating animal body tissue, and a treatment of fragmenting animal body tissue, an alkali extraction step in which the pre-treated animal body tissue is immersed in an alkaline solution and collagen and other unwanted protein are separated by filtration, a filtrate recovery step of obtaining a filtrate containing a water-soluble elastin by filtration by repeating a predetermined number of times an alkali dissolution step of dissolving the residue after the alkali extraction step with an alkali, and a water-soluble elastin formation step of forming a water-soluble elastin from the filtrate. As the alkali used in the alkali dissolution step, any one of sodium hydroxide, potassium hydroxide, calcium hydroxide, and barium hydroxide, or a mixture thereof is preferable.

Unlike the first process, in which collagen and other unwanted protein is removed from tissue to thus give an insoluble elastin and subsequently this insoluble elastin is solubilized to obtain a water-soluble elastin, this procedure is a process in which a water-soluble elastin is directly obtained from tissue without obtaining an insoluble elastin. That is, it is a process for obtaining a water-soluble elastin by immersing delipidated, fragmented, and salt-treated animal body tissue in a 0.03 to 0.5 mol per L, and preferably 0.05 to 0.3 mol per L, alkaline solution at 90° C. to 105° C. for 5 to 60 minutes, thus giving treated tissue from which collagen and unwanted protein other than elastin have been removed, and subsequently by immersing this treated tissue in a 0.05 to 5 mol per L, and preferably 0.05 to 2 mol per L, alkaline solution (the concentration of the alkaline solution being higher) at 90° C. to 105° C. for 5 to 420 minutes, and preferably 10 to 240 minutes (the time being longer), to thus dissolve it.

The water-soluble elastin obtained by the first or second process is then subjected to for example a dialysis treatment to thus remove a low molecular weight fraction, thus giving a high molecular weight water-soluble elastin that can preferably be used in the present invention. Removing a low molecular weight fraction enables a water-soluble elastin advantageously having a superior ability to coacervate to be obtained.

In production of the chemically modified water-soluble elastin of the present invention, first, at least some of the primary amines and secondary amines contained in a water-soluble elastin molecule are subjected to N-acylation, and preferably N-acetylation, thus giving an N-acylated water-soluble elastin. Among amino acid residues forming elastin, as amino acids having a reactive primary amine or secondary amine (basic amino acid), lysine, arginine, and histidine can be cited, and as a primary amine contained in a water-soluble elastin molecule, a terminal amino group is also included.

In the present invention, at least some of the primary amines and secondary amines contained in a high molecular weight water-soluble elastin molecule are N-acetylated. The N-acetylation is preferably carried out by means of an acetylation reagent such as acetic anhydride, and the degree of N-acetylation is at least 80 mole % when expressed as a degree of modification represented by Equation (1) below, more preferably at least 90 mole %, and particularly preferably at least 95 mole %.

$$\text{Degree of modification(mole \%)} = (1 - B/A) \times 100 \tag{1}$$

In the Equation, A denotes a value obtained by subtracting the average value of the absorbance (wavelength 345 nm) of a blank from the average value of the absorbance of the water-soluble elastin. B denotes a value obtained by subtracting the average value of the absorbance (wavelength 345 nm) of a blank from the average value of the absorbance of the N-acetylated water-soluble elastin.

In the case of N-acylation other than N-acetylation, the degree may be determined optically under the same conditions.

In order to N-acetylate 90 mole % or more of the primary amines and secondary amines contained in a water-soluble elastin, it is preferable to use 0.5 to 5 mmol of acetic anhydride per g of the water-soluble elastin.

In the present invention, a chemically modified water-soluble elastin is obtained by coupling at least some of the carboxyl groups contained in the N-acylated, and preferably N-acetylated, water-soluble elastin molecule so obtained with an amino acid alkyl ester. In the present invention, a lower alkyl ester having 1 to 4 carbons is preferable, and a methyl ester is particularly preferable. One such as a benzyl ester may also be used. Among amino acid residues forming elastin, as an amino acid having a carboxyl group (acidic amino acid), there are aspartic acid and glutamic acid, and as a carboxyl group contained in the water-soluble elastin molecule, a terminal carboxyl group is also included.

In the present invention, it is preferable that almost all of the carboxyl groups contained in the N-acylated, and preferably N-acetylated, water-soluble elastin molecule are modified by coupling with an amino acid alkyl ester. Here, 'almost all' means that the percentage reaction is at least 90 mole %. The percentage reaction is preferably at least 95 mole %. When carrying out a coupling reaction it is preferable to use, per mole equivalent of the water-soluble elastin, an excess amount of a coupling agent such as a carbodiimide or a condensing agent, more preferably 60 to 200 mole equivalent, and yet more preferably 80 to 120 mole equivalent. When 60 to 200 mole equivalent of a highly active coupling agent is used, a percentage reaction of 90 mole % or higher is achieved.

In order to amidate 90 mole % or more of the carboxy groups contained in a water-soluble elastin, it is preferable to use 0.3 to 1 mmol of a coupling agent such as a carbodiimide per g of water-soluble elastin starting material.

Figure 5:
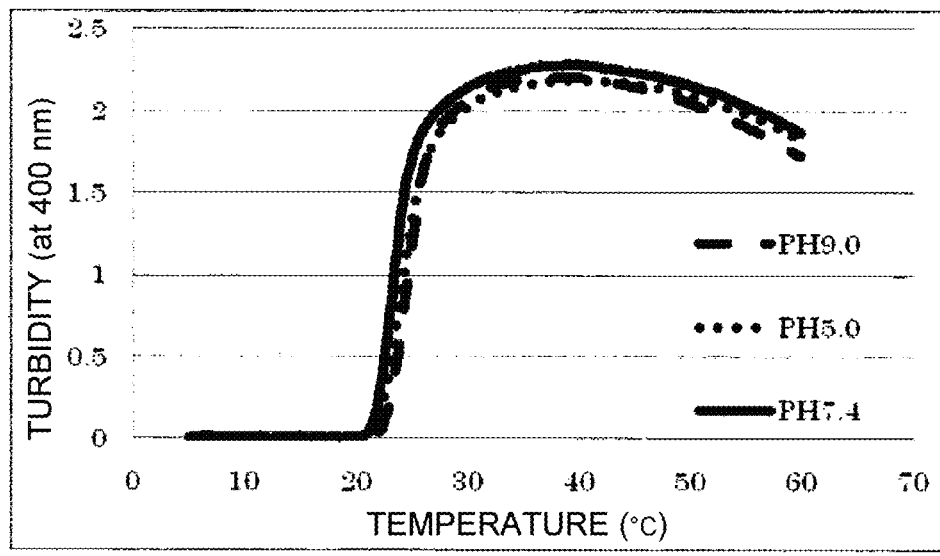
FIG. 5 shows a diagram showing turbidity curves of the chemically modified water-soluble elastin N-Ac-Ela-O-Gly-OMe under various pH conditions (solvent: PBS).

As shown in FIG. 5, since the turbidity curve does not change when the pH is changed in a range of 5 to 9, the interpretation is that almost all of the carboxyl groups have been modified.

Instead of amidating the carboxy groups after N-acylating the amino groups of a water-soluble elastin, the amino groups of a water-soluble elastin may be N-acylated after amidating the carboxy groups.

In the present invention, a composition comprising a chemically modified water-soluble elastin is used as a temperature responsive sheet. A component other than the chemically modified water-soluble elastin may be used in combination as long as the temperature responsive function is not impaired, but it is preferable for the temperature responsive sheet to employ only a chemically modified water-soluble elastin or only a polypeptide having a peptide sequence that is present in elastin.

Figure 3:
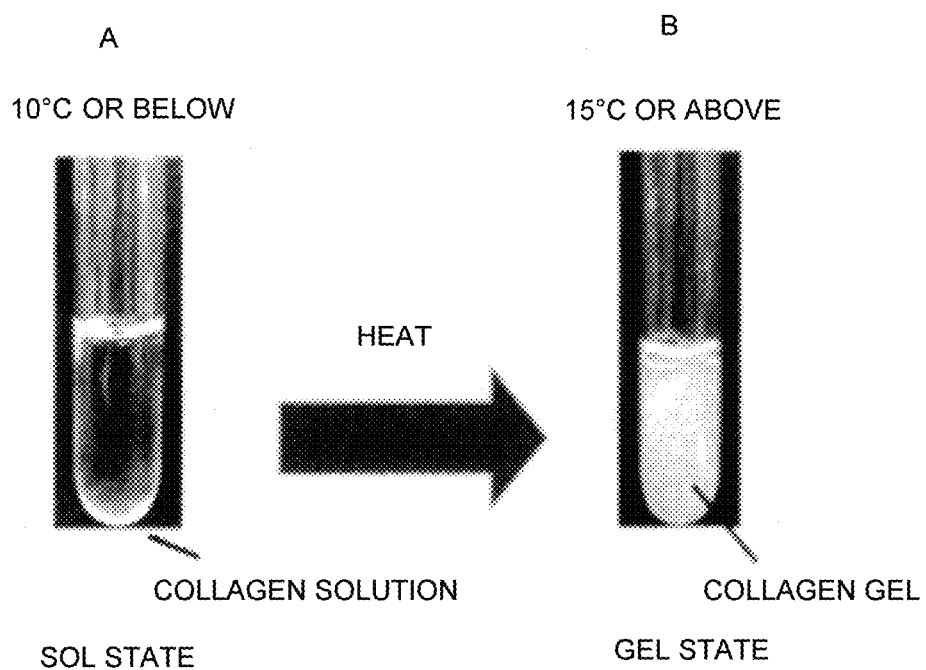
FIG. 3 shows a diagram showing gelling of collagen.

FIG. 3 is a diagram showing gelling of collagen in a test tube. As shown in A of FIG. 3, a collagen solution is in a sol state at 10° C. or below. As shown in B of FIG. 3, when heated to 15° C. or above, the collagen solution becomes cloudy and gels, thus giving a collagen gel. This collagen gel does not return to the original sol state even when cooled.

Figure 4:
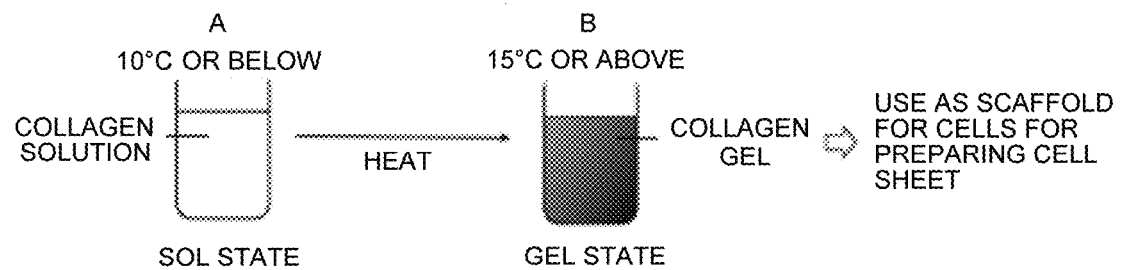
FIG. 4 shows a diagram schematically showing gelling of collagen.

FIG. 4 is a diagram schematically showing gelling of collagen. A collagen gel is used as a scaffold for cells when preparing a cell sheet. The scaffold is used for retaining the shape of the cell sheet. As is well known to a person skilled in the art, a scaffold for cells means an extracellular matrix necessary for the survival of normal animal cells (epithelial cells, endothelial cells, fibroblasts, smooth muscle cells, etc.). Extracellular matrix types can be roughly divided into a collagen group, a noncollagenous sugar protein group, an elastin group, and a proteoglycan group, and collagen, fibronectin, laminin, polylysine, and gelatin can be cited as preferred specific examples.

Figure 10:
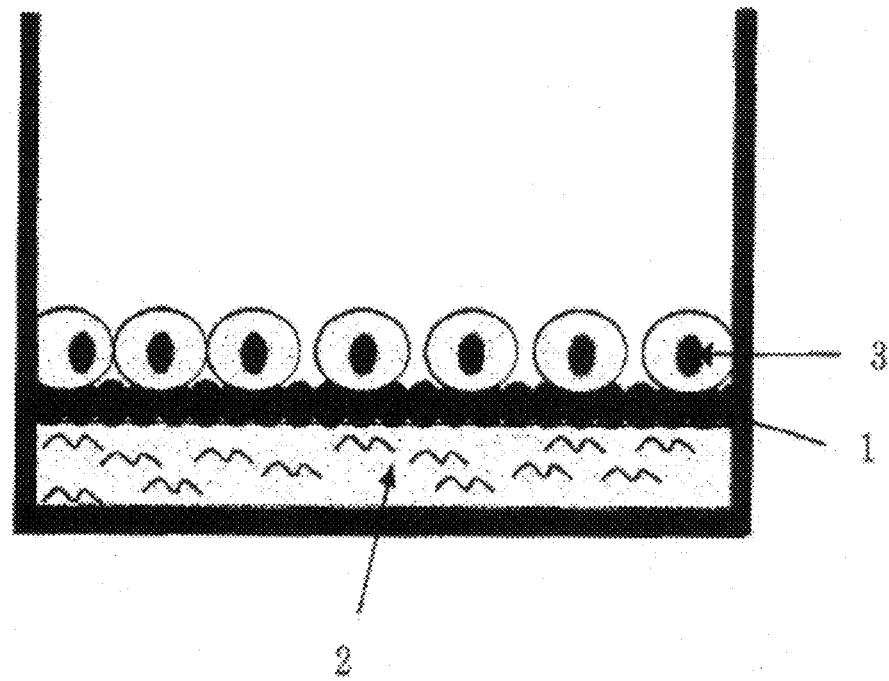
FIG. 10 shows a diagram schematically showing a state in which a collagen gel is prepared on a coacervate of the chemically modified water-soluble elastin N-Ac-Ela-O-Gly-OMe and fibroblasts are seeded on the gel.
Figure 13:
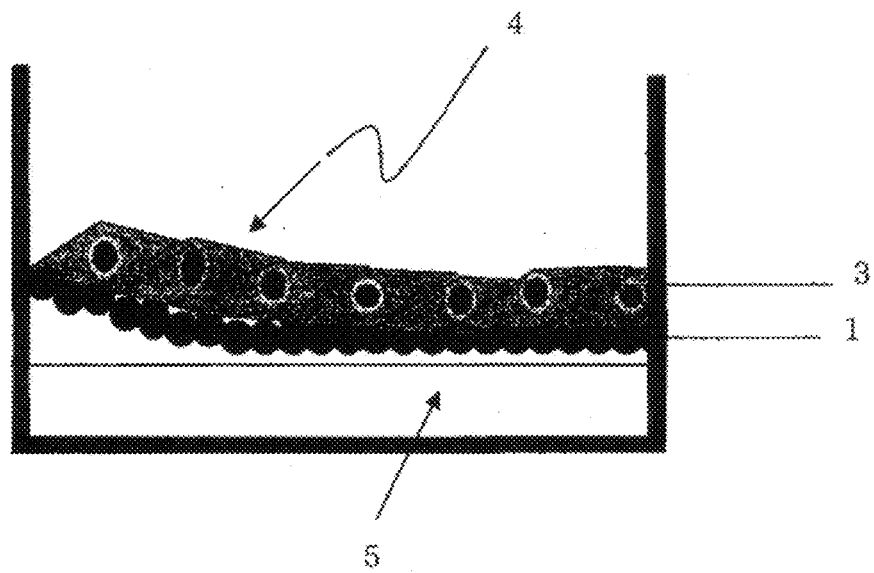
FIG. 13 shows a diagram schematically showing a state in which a coacervate of the chemically modified water-soluble elastin N-Ac-Ela-O-Gly-OMe has dissolved and a cell sheet comprising the collagen gel and fibroblasts is being peeled off.

As the collagen that is used in the production of a cell sheet of the present invention, any collagen that is known as being for medical use may be used. Collagen that is suitable for medical use is usually obtained, as a viscous collagen solution or as a solid obtained by drying this solution, by a method in which it is extracted, mainly from animals as a source, by means of an enzyme, etc. under acidic, alkaline, neutral, etc. conditions. Furthermore, by subjecting the collagen to a pepsin treatment to thus remove antigenicity-exhibiting sites, a collagen (atelocollagen) that is free from antigenicity when grafted within the body or on the body surface and is more suitable as a medical substrate may be obtained. Representative examples of collagens used in the present invention include solubilized collagens such as an acid-solubilized collagen, an alkali-solubilized collagen, an enzyme-solubilized collagen, and a neutral-solubilized collagen, and an atelocollagen that has been subjected to a treatment involving removing telopeptides, which are epitopes of collagen, at the same time as the solubilization treatment is particularly suitable. A collagen solution is in a sol state at low temperature and gels when heated to become a collagen gel. As shown in FIGS. 10 and 13, since this collagen gel does not return to the original sol state even when cooled, it can be used as a scaffold for cells in the production of a cell sheet.

The process for producing a cell sheet of the present invention comprises a step of forming a temperature responsive sheet comprising a chemically modified water-soluble elastin above a support, a step of producing a cell sheet by culturing specific cells above the temperature responsive sheet, and a step of subsequently separating the temperature responsive sheet and the cell sheet at 1° C. to 20° C., and preferably 5° C. to 15° C., which is below the culturing temperature for the cells. It is preferable to add, prior to the step of producing a cell sheet, a step of providing above the temperature responsive sheet a layer of a collagen gel, etc. as a scaffold, which is an extracellular matrix, and specific cells are cultured on this layer of collagen gel, etc.

Each of the steps is explained below.

The step of forming a temperature responsive sheet comprising a chemically modified water-soluble elastin above a support is now explained.

The support, which is a substrate for producing a temperature responsive sheet, is not particularly limited, and an inactive support that does not adversely affect cell culturing can be used. Examples of such a support include glass and a resin such as polystyrene (PS) normally used as culturing containers.

The temperature responsive sheet comprising a chemically modified water-soluble elastin preferably comprises a chemically modified water-soluble elastin as a main component (at least 90 wt %), and more preferably comprises only a chemically modified water-soluble elastin. The thickness of this sheet is preferably on the order of nm to μm, and more preferably 50 nm to 500 μm. In other words, the dry coat weight is preferably 0.01 to 100 g/m$^2$. The incubation temperature for forming a coacervate is preferably 40° C. to 80° C., and more preferably 50° C. to 70° C. Drying is preferably carried out at 35° C. to 40° C. for 5 to 20 minutes.

A step of providing a collagen gel layer on the temperature responsive sheet is now explained.

The thickness of the collagen gel layer is preferably about 1 to 1,000 μm, and more preferably about 10 to 500 μm. The incubation temperature for forming a film is preferably 30° C. to 40° C., and more preferably around 37° C. The concentration of the solution is preferably 0.1 mg/mL to 10 mg/mL, and more preferably 0.5 mg/mL to 2 mg/mL.

The step of preparing a cell sheet by culturing specific cells above the temperature responsive sheet is now explained. Examples of specific cells include epithelial cells, endothelial cells, fibroblasts, and smooth muscle cells. The method for cell culturing is a standard method.

The cell sheet may be a single layer or multiple layers. In the case of multiple layers, they may be the same cells or different types of cells.

In order to promote the preparation of a cell sheet, culturing may be carried out by adding to a medium a growth factor that promotes culturing of cells, such as a vascular endothelial growth factor, a fibroblast growth factor, an epidermal growth factor, an insulin-like growth factor, a transforming growth factor, or a platelet-derived growth factor.

The step of separating the temperature responsive sheet and the cell sheet is explained.

This step is a step of separating the temperature responsive sheet and the cell sheet under conditions of no greater than the culturing temperature for the cells. Here, 'being no greater than the culturing temperature' means that when the culturing temperature is 37° C., it is preferably 1° C. to 20° C., and more preferably 10° C. to 15° C.

FIG. 10 is a diagram schematically showing a state in which a collagen gel having fibroblasts seeded thereon is above a coacervate of the chemically modified water-soluble elastin N-Ac-Ela-O-Gly-OMe. In FIG. 10, 1 denotes the collagen gel, 2 denotes the N-Ac-Ela-O-Gly-OMe coacervate (temperature responsive sheet), and 3 denotes the fibroblasts. Following the step of preparing a cell sheet by culturing the fibroblasts, a step of separating the temperature responsive sheet 2, which comprises the chemically modified water-soluble elastin, and the cell sheet 3 is carried out by decreasing the temperature to no greater than the culturing temperature for the fibroblasts.

Figure 11:
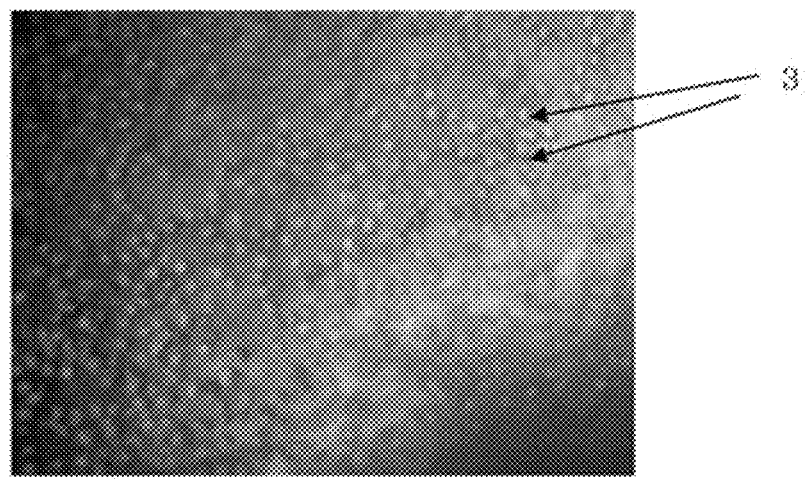
FIG. 11 shows an optical microscope photograph of a fibroblast spherical state immediately (0 hours) after seeding fibroblasts on a collagen gel prepared on a coacervate of the chemically modified water-soluble elastin N-Ac-Ela-O-Gly-OMe.
Figure 12:
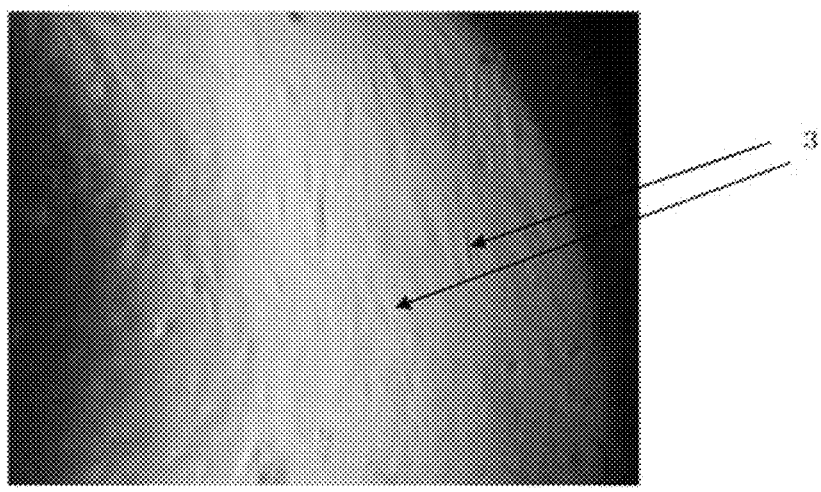
FIG. 12 shows an optical microscope photograph of a fibroblast spindle-shaped state 24 hours after culturing fibroblasts seeded on a collagen gel prepared on a coacervate of the chemically modified water-soluble elastin N-Ac-Ela-O-Gly-OMe.

FIG. 11 is an optical microscope photograph showing one example of a spherical state of fibroblasts immediately after being seeded on a collagen gel (0 hours), in which 3 denotes fibroblasts. FIG. 12 is a optical microscope photograph showing a spindle-shaped state of fibroblasts when culturing 24 hours after being seeded on a collagen gel, in which 3 denotes fibroblasts.

FIG. 13 is a diagram schematically showing a state in which a coacervate of the chemically modified water-soluble elastin N-Ac-Ela-O-Gly-OMe has dissolved, and a cell sheet comprising a collagen gel and fibroblasts is being peeled off.

1 denotes the collagen gel, 3 denotes the fibroblasts, 4 denotes the cell sheet that is being peeled off, and 5 denotes the N-Ac-Ela-O-Gly-OMe coacervate (temperature responsive sheet) in a dissolved state.

In the present invention, instead of using a chemically modified water-soluble elastin, a polypeptide chemically synthesized based on a peptide sequence that is present in an elastin may be used.

Examples of the peptide sequence that is present in an elastin include poly(VPGVG) and poly(VPGG) (SEQ ID NO:2). These polypeptides are peptides present in common in elastins of mammals such as humans, swine, or cattle, and are polypeptides having very few problems in terms of toxicity, immunological aspects, etc. Furthermore, examples of elastin-derived polypeptides include poly(PGVGV) (SEQ ID NO:3), poly(GVGVP) (SEQ ID NO:4), poly(VGVPG) (SEQ ID NO:5) and poly(GVPGV) (SEQ ID NO:6), which are permutation polypeptides of poly(VPGVG) (SEQ ID NO:1), and poly(PGGV) (SEQ ID NO:7), poly(GGVP) (SEQ ID NO:8) and poly(GVPG) (SEQ ID NO:9), which are permutation polypeptides of poly(VPGG). Furthermore, examples of the polypeptide of the present invention include poly($X_1PX_2X_3X_4$), which is a poly(VPGVG) (SEQ ID NO:1) substitute, poly($PX_2X_3X_4X_1$), which is a poly(PGVGV) (SEQ ID NO:3) substitute, poly($X_2X_3X_4X_1P$), which is a poly(GVGVP) (SEQ ID NO:4) substitute, poly($X_3X_4X_1PX_2$), which is a poly(VGVPG) (SEQ ID NO:5) substitute, poly($X_4X_1PX_2X_3$), which is a poly(GVPGV) (SEQ ID NO:6) substitute, poly($X_1PX_2X_3$), which is a poly(VPGG) (SEQ ID NO:2) substitute, poly($PX_2X_3X_1$), which is a poly(PGGV) (SEQ ID NO:7) substitute, poly($X_2X_3X_1P$), which is a poly(GGVP) (SEQ ID NO:8) substitute, and poly($X_3X_1PX_2$), which is a poly(GVPG) (SEQ ID NO:9) substitute. In the present invention, a polypeptide means one having a molecular weight of at least about 3,000, and preferably 5,000 to 100,000. Furthermore, $X_1$, $X_2$, $X_3$, and $X_4$ may be any of the approximately 20 types of amino acids that form proteins.

Figure 14:
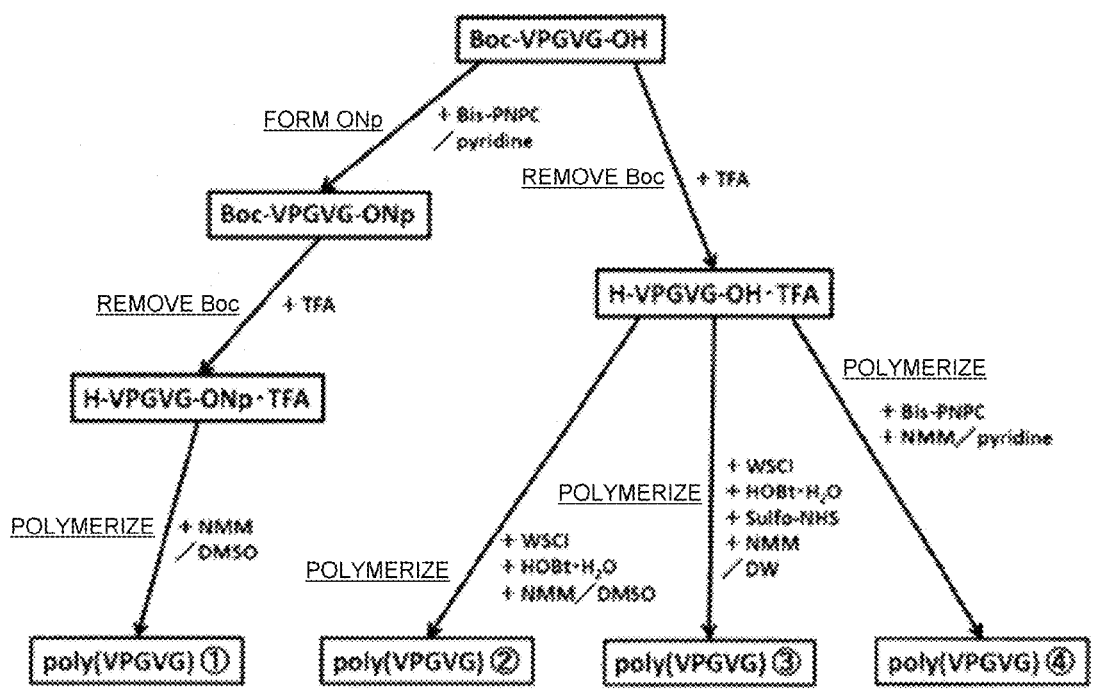
FIG. 14 a diagram showing a process for producing (polymerizing) four types of poly(VPGVG) (SEQ ID NO: 1).

FIG. 14 is a flow chart showing four types of processes (polymerization) for producing poly(VPGVG) (SEQ ID NO:1). ONp denotes p-nitrophenyl ester, TFA denotes trifluoroacetic acid, DMSO denotes dimethyl sulfoxide, NMM denotes N-methylmorpholine, WSCI denotes a water-soluble carbodiimide, HOBt.$H_2O$ denotes 1-hydroxybenzotriazole monohydrate, Sulfo-NHS denotes sulfosuccinimide, DW denotes distilled water, and Bis-PNPC denotes bis(4-nitrophenyl) carbonate.

EXAMPLES

The present invention is explained below specifically by reference to Examples. The various measurement methods were as follows.

—Degree of Modification by N-Acetylation—

The degree of modification by N-acetylation was measured and calculated by a TNBS (2,4,6-trinitrobenzenesulfonic acid) method as follows. 1 mL of each of a 4% sodium bicarbonate solution and a 0.1% TNBS aqueous solution were added to a 1 mg/mL N-acetylated water-soluble elastin (N-Ac-Ela) aqueous solution. One to which only 1 mL of each of the 4% sodium bicarbonate solution and the 0.1% TNBS aqueous solution had been added was defined as a blank (n=3). The solutions thus prepared were shielded from light by aluminum foil, and a reaction was carried out at 40° C. for 2 hours. After the reaction was completed, 1 mL of 10% SDS (sodium dodecylsulfate) and 0.5 mL of 1N HCl were added to 0.17 mL of the solution thus prepared, and the absorbance at 345 nm was measured for each solution. The degree of modification was determined from the equation below.

Degree of modification(mole %)=(1−B/A)×100

In the Equation, A denotes the value obtained by subtracting the average value of the absorbance (wavelength 345 nm) of the blank from the average value of the absorbance of the elastin aqueous solution, and B denotes the value obtained by subtracting the average value of the absorbance (wavelength 345 nm) of the blank from the average value of the absorbance of the N-Ac-Ela aqueous solution.

—Turbidity Measurement—

A chemically modified water-soluble elastin, an elastin-derived polypeptide, and a type I collagen were dissolved in phosphate buffered physiological saline (phosphate buffered saline; PBS solution) at 5° C. while taking into consideration physiological conditions, and the solutions were subjected to turbidity measurement at a wavelength of 400 nm with a temperature change of 0.5° C./min under a flow of nitrogen. As measurement equipment, a Peltier type temperature controller-equipped spectrophotometer (Ubest-50, JASCO Corporation) was used.

—Preparation of Porcine Water-Soluble Elastin—

1) Isolation of Porcine Insoluble Elastin

Collagen and unwanted NaCl-soluble and NaOH-soluble protein other than elastin were removed by extraction from delipidated porcine aorta tissue in accordance with the procedure below.

Porcine aorta tissue (body tissue) was used; as a pre-treatment, a treatment involving removing unwanted portions was carried out by scraping off portions having a low elastin content such as fat and muscle attached to the tissue using a knife etc., and subsequently a fragmentation treatment was carried out by homogenizing the body tissue using a homogenizer. The homogenized body tissue was subjected to a delipidation treatment by treating it with hot water, a hot dilute aqueous alkali solution, or an organic solvent such as acetone, and then dried. Subsequently, about 10 times by volume of the delipidated and dried tissue weight of 1M sodium chloride was added, and stirring was carried out at room temperature for 1 hour, thus extracting and removing unwanted NaCl-soluble protein. This procedure was repeated five times, washing with distilled water was then carried out, and the water was drained by centrifugation (3,000 rpm, 5 minutes).

A step of removing collagen and unwanted protein other than elastin was carried out in which about 10 times by volume of the weight of the delipidated and salt-treated body tissue obtained (10 mL per g of weight) of a 0.1N sodium hydroxide aqueous solution was added, and stirring was carried out at 100° C. for 15 minutes. The body tissue and the alkaline solution were then separated. The separated alkaline solution was subjected to quantitative measurement of total protein by the biuret method, and the above procedure was repeated until the total protein mass contained in the alkaline solution became no greater than 0.1 mg/mL. The sample was then cooled and washed by centrifugation (5,000 rpm, 20 minutes), and the residue was dried, thus giving an insoluble elastin.

2) Preparation of Porcine High Molecular Weight Water-Soluble Elastin 10 times by volume of the dry weight of the porcine insoluble elastin of 0.5 N NaOH was added, and stirring was carried out in an oil bath at 100° C. 30 minutes. After the reaction, the solution was quickly cooled with ice and neutralized with acetic acid, hydrochloric acid, or citric acid. The sample was subsequently subjected to dialysis for 1 week using a dialysis membrane having a molecular weight cut-off of 6,000 to 8,000, and the solution on the inside of the dialysis membrane was lyophilized, thus giving a porcine high molecular weight water-soluble elastin having a main molecular weight of about 30,000 to 300,000.

—Preparation of Chemically Modified Porcine High Molecular Weight Water-Soluble Elastin—

The porcine high molecular weight water-soluble elastin was subjected to N-acetylation in accordance with the procedure below, and then to coupling using an amino acid (glycine) methyl ester, thus preparing a chemically modified porcine high molecular weight water-soluble elastin (N-Ac-Ela-O-Gly-OMe).

1) N-Acetylation of Porcine High Molecular Weight Water-Soluble Elastin

Pyridine (100 equivalents) and acetic anhydride (100 equivalents) were added to a solution of a small amount of the porcine high molecular weight water-soluble elastin so obtained in trifluoroethanol, and stirring was carried out at room temperature. After checking by a ninhydrin test if acetylation had progressed quantitatively, the sample was vacuum-concentrated using a rotary evaporator. The N-acetylation was repeated several times until the degree of modification of amino groups, etc. attained 95 mole % by the TNBS method. This solution was then subjected to dialysis for 1 week so as to remove solvent, unreacted reagent, etc., and lyophilized, thus giving an N-acetylated water-soluble elastin. The degree of modification by the TNBS method was 97 mole %.

2) Preparation of Chemically Modified Water-Soluble Elastin (N-Ac-Ela-O-Gly-OMe)

A water-soluble carbodiimide (100 equivalents) was added to a solution of a small amount of the N-acetylated water-soluble elastin (N-Ac-Ela) in dimethylformamide, and stirring was carried out at room temperature for 15 minutes. After that, a solution of small amounts of H-Gly-OMe.HCl (100 equivalents) and triethylamine (100 equivalents) in dimethylformamide was added, and stirring was carried out at room temperature for a whole day and night. Subsequently, the sample was vacuum-concentrated using a vacuum pump, subjected to dialysis for 1 week so as to remove solvent, unreacted reagent, etc., and lyophilized, thus giving a chemically modified water-soluble elastin (N-Ac-Ela-O-Gly-OMe).

3) Turbidity Measurement Using N-Ac-Ela-O-Gly-OMe 1.0 mg of the N-Ac-Ela-O-Gly-OMe thus obtained was dissolved in each of PBS solutions having a pH of 5.0, 7.4, and 9.0 at 5° C., and the turbidity at a wavelength of 400 nm was measured in a temperature range of 5° C. to 60° C. at a temperature increase of 0.5° C./min. The results are shown in FIG. 5. In FIG. 5, the turbidity curves at pHs of 5.0, 7.4, and 9.0 of N-Ac-Ela-O-Gly-OMe (1.0 mg/mL) showed that the curves were substantially the same for acidic, neutral, and alkaline conditions. It could be confirmed from this result that, in addition to protection of the amino groups by N-acetylation, modification of the carboxyl groups by coupling with H-Gly-OMe eliminated the charge of the water-soluble elastin, and the N-Ac-Ela-O-Gly-OMe could be synthesized substantially quantitatively.

—Measurement of Reversible Turbidity Curve of N-Ac-Ela-O-Gly-OMe—

Figure 6:
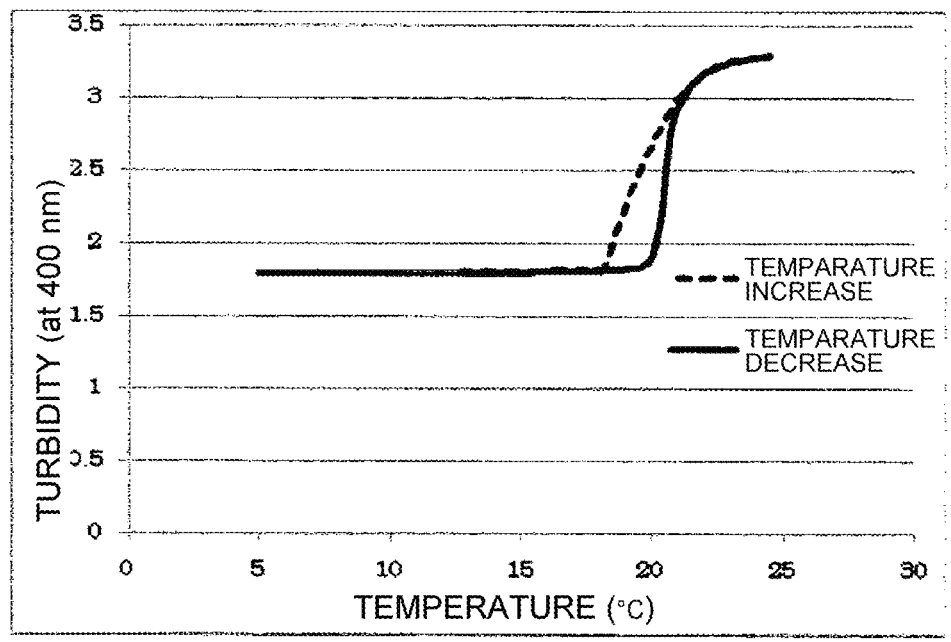
FIG. 6 shows a diagram showing a reversible turbidity curve of the chemically modified water-soluble elastin N-Ac-Ela-O-Gly-OMe.

A 30 mg/mL solution of N-Ac-Ela-O-Gly-OMe was prepared by dissolving it in a PBS solution (pH 7.4) at 5° C., and turbidity measurement was carried out when the temperature was increased and decreased in a temperature range of 5° C. to 25° C. under a flow of nitrogen with a temperature change of 0.5° C./min. The results are shown in FIG. 6. It can be seen from FIG. 6 that with regard to the turbidity curve of N-Ac-Ela-O-Gly-OMe, the turbidity curve accompanying increase in temperature substantially coincided with the turbidity curve accompanying decrease in temperature and it was reversible. The results of FIG. 6 and FIGS. 1 and 2 indicate that due to coacervation the N-Ac-Ela-O-Gly-OMe became cloudy when heated, a coacervate was formed at 37° C. and a pH of 7.4, which were the conditions for cell culturing, and there was a return to the original transparent solution state at 20° C. or below.

—Indentation Test on N-Ac-Ela-O-Gly-OMe Coacervate—

Figure 7:
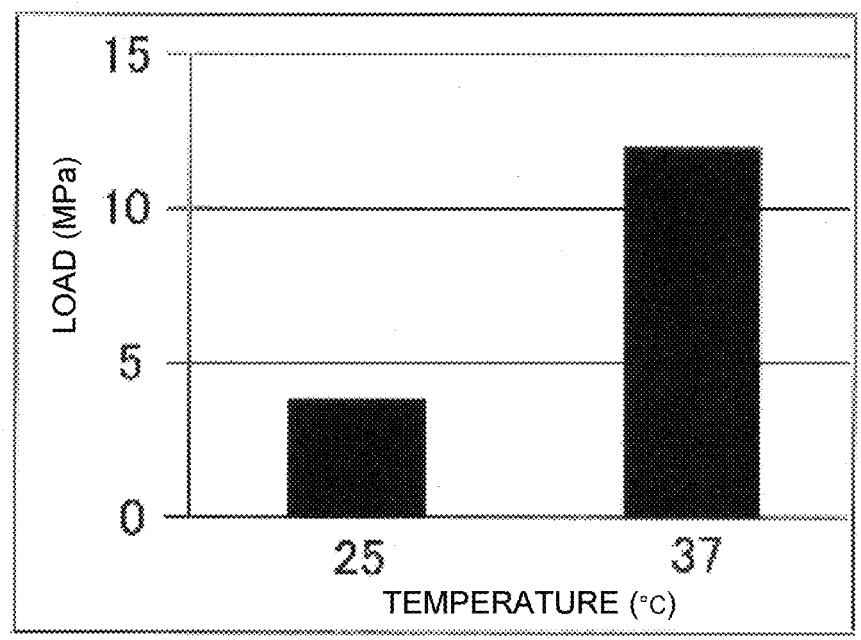
FIG. 7 shows a diagram showing the hardness of a coacervate of the chemically modified water-soluble elastin N-Ac-Ela-O-Gly-OMe.

The N-Ac-Ela-O-Gly-OMe was dissolved in a PBS solution (pH 7.4) at 5° C. in a vial so as to give 200 mg/mL. Subsequently, this was heated to 50° C., it became cloudy, and was allowed to stand at that temperature for 24 hours, resulting in separation into two layers. The upper layer equilibrium solution was removed, the surface of the lower layer coacervate was dried for about 10 minutes, and indentation tests were carried out using a RHEONER-II-CREEP-METER (RE2-3305B, YAMADEN) while maintaining the temperature at 25° C. and 37° C. The hardness of the coacervate was expressed as a load (MPa) with respect to indentation. The results are shown in FIG. 7. It was confirmed from FIG. 7 that the N-Ac-Ela-O-Gly-OMe coacervate became harder at the high temperature of 37° C. compared with 25° C. That is, it was found that the coacervate maintained a hard state under cell culturing conditions of 37° C., but became soft when cooled to 25° C. and attained a state in which it dissolved easily. Furthermore, at 15° C. the coacervate had dissolved and measurement could not be carried out.

—Irreversible Turbidity Curve of Collagen—

Figure 8:
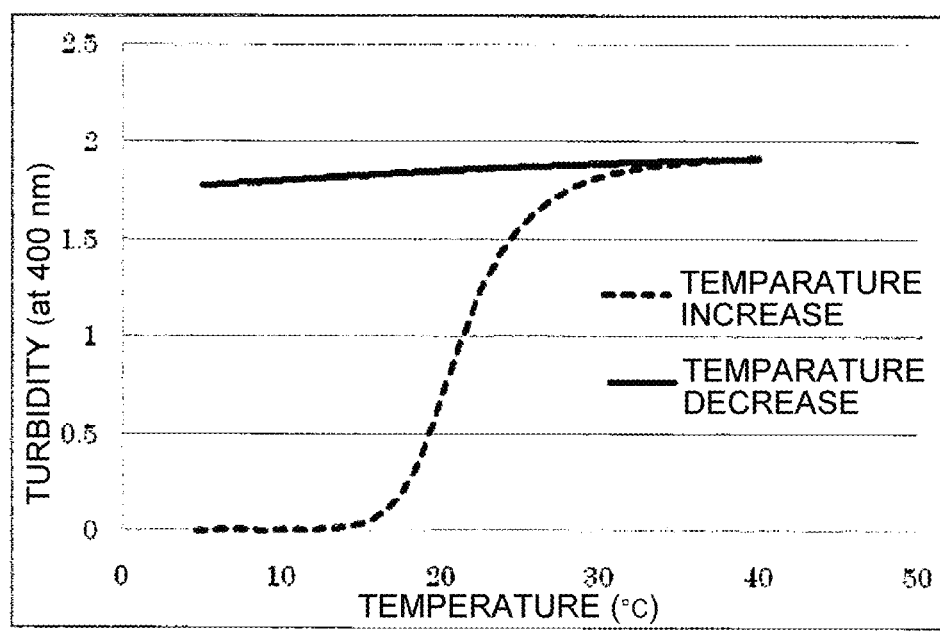
FIG. 8 shows a diagram showing an irreversible turbidity curve of type I collagen.

A 1 mg/mL PBS solution (pH 7.4) of type I collagen was prepared at 5° C., and turbidity measurement was carried out when the temperature was increased and decreased in a temperature range of 5° C. to 40° C. under a flow of nitrogen with a temperature change of 0.5° C./min. The results are shown in FIG. 8. It was found from FIG. 8 that, with regard to the turbidity curve of the type I collagen, the turbidity curve accompanying increase in temperature did not coincide with the turbidity curve accompanying decrease in temperature, and it was irreversible. The result of FIG. 8 and FIGS. 3 and 4 indicate that the type I collagen changed from a sol to a gel accompanying increase in temperature, it formed a gel at 37° C. and a pH of 7.4, which were the conditions for cell culturing, did not return to the original sol state even when cooled, and remained gelled.

—Cell Proliferation Experiment on Collagen Gel—

Figure 9:
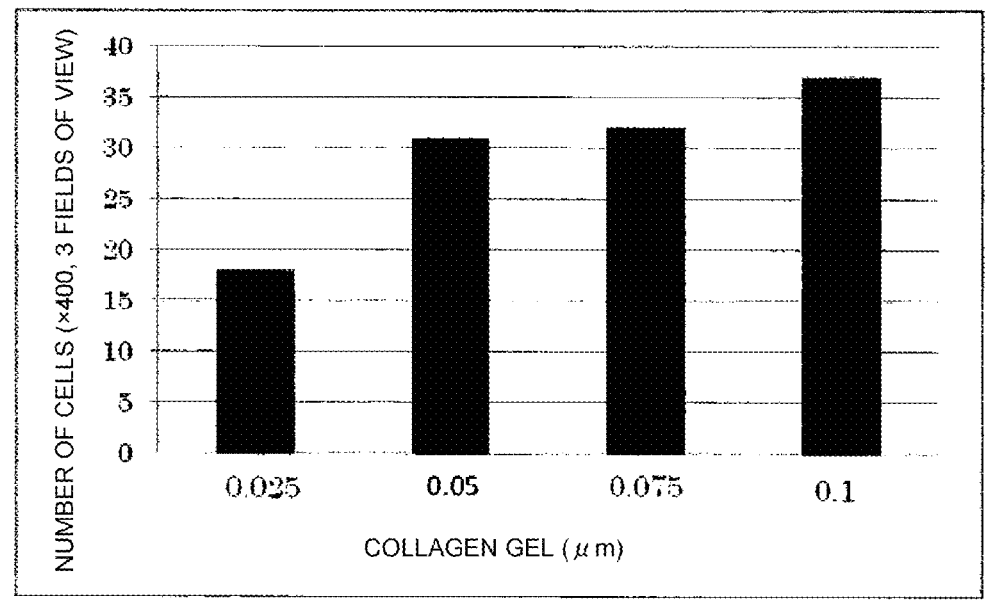
FIG. 9 shows a diagram showing cell proliferation on a type I collagen gel.

50 µL of each of 0.5 mg/mL, 1.0 mg/mL, 1.5 mg/mL, and 2.0 mg/mL PBS solutions (pH 7.4) of type I collagen were added to a 96 well culture dish and incubated for 1 hour (37° C., in 5% carbon dioxide), and the collagen gel thus prepared in each well was seeded with 100 µL of $2.0 \times 10^4$ cells/mL human skin fibroblasts suspended in Dulbecco's-Modified-Eagle-Medium (DMEM) supplemented with 0.5% fetal bovine serum. After culturing for two days (37° C., in 5% carbon dioxide), the medium was exchanged, culturing was carried out for a further two days, and the number of cells was counted (×400, 3 fields of view). The results are shown in FIG. 9. It can be seen from FIG. 9 that the larger the amount of collagen gel, the larger the number of cells.

—Preparation of Cell Sheet—

The N-Ac-Ela-O-Gly-OMe was dissolved in a PBS solution (pH 7.4) to give 30 mg/mL, the solution was sterilized by passing it through a 0.22 µm Filter-Unit sterilization filter, and 100 µL was pipetted into each well of a 96 well culture dish and incubated for 24 hours (60° C., in 5% carbon dioxide), thus separating it into two layers. Subsequently, the upper layer equilibrium solution was removed, and the surface of the lower layer coacervate was dried at 37° C. for about 10 minutes. Subsequently, a 1 mg/mL PBS solution of type I collagen was prepared (sterilized), and 100 µL thereof was added to each of the coacervates and incubated for 1 hour (37° C., in 5% carbon dioxide), thus preparing a collagen gel film. The collagen gel film of each well was seeded with 100 µL of $2.0 \times 10^4$ cells/mL human skin fibroblasts suspended in DMEM medium supplemented with 10.0% fetal bovine serum, and culturing was carried out in an incubator with 5% carbon dioxide at 37° C. for 24 hours. The results of examining the state of the cells in this process using an optical microscope are shown in FIG. 11 to FIG. 12.

It was confirmed by the naked eye that the collagen gel seeded with the fibroblasts was present on the N-Ac-Ela-O-Gly-OMe coacervate. FIG. 10 schematically shows the state in which the collagen gel was prepared on the N-Ac-Ela-O-Gly-OMe coacervate and fibroblasts were seeded on the gel. In this state, the cells were attached to the gel prior to adhering thereto. In FIG. 10, 1 denotes collagen gel, 2 denotes N-Ac-Ela-O-Gly-OMe coacervate, and 3 denotes fibroblasts prior to adhering. FIG. 11 is an optical microscope photograph showing that cells immediately after seeding (0 hours) were present on the collagen gel in a state (spherical) in which they were attached prior to adhering. In FIG. 11, 3 denotes fibroblasts prior to adhering. FIG. 12 is an optical microscope photograph showing that fibroblasts after 24 hours of culturing were present on the collagen gel in a spindle-shaped state, suggesting adhesion, spreading, and proliferation. In FIG. 12, 3 denotes fibroblasts that are adhering, spreading, and proliferating.

—Peeling Off Cell Sheet—

A collagen gel was prepared on an N-Ac-Ela-O-Gly-OMe coacervate, fibroblasts were seeded thereon, culturing was carried out for 24 hours to thus prepare a cell sheet, following this by cooling to 15° C. and incubating for 30 minutes the N-Ac-Ela-O-Gly-OMe coacervate was dissolved, and a cell sheet comprising the fibroblasts and the collagen gel was peeled off. A state in which the adhered, spread, and proliferated cell sheet on the collagen gel had peeled off could be observed by the naked eye. FIG. 13 is a diagram schematically showing a state in which the N-Ac-Ela-O-Gly-OMe coacervate has dissolved and a cell sheet comprising the collagen gel and fibroblasts is being peeled off. In FIG. 13, 1 denotes the collagen gel, 3 denotes the fibroblasts that are adhering, spreading, and proliferating, 4 denotes the cell sheet, and 5 denotes the state in which the N-Ac-Ela-O-Gly-OMe coacervate has dissolved and disappeared. By decreasing the temperature in this way the N-Ac-Ela-O-Gly-OMe coacervate was dissolved, and a cell sheet comprising the fibroblasts and the collagen gel was easily produced and recovered without being damaged.

The N-Ac-Ela-O-Gly-OMe was dissolved in a PBS solution (pH 7.4) to give 10 mL of a 30 mg/mL solution, the solution was sterilized by passing it through a 0.22 µm Filter-Unit sterilization filter, and 3.6 mL was pipetted onto each of culture dishes having a diameter of 6 cm (coat weight 38 g/m$^2$) and incubated for 24 hours (60° C., in 5% carbon dioxide), thus separating it into two layers. Subsequently, the upper layer equilibrium solution was removed, and the surface of the lower layer coacervate film (100 to 200 µm thick) was dried at 37° C. for about 10 minutes. Subsequently, 10 mL of a 1 mg/mL PBS solution of type I collagen was prepared (sterilized), and 3.6 mL thereof was added onto each of the coacervates (coat weight 1.3 g/m$^2$) and incubated for 1 hour (37° C., in 5% carbon dioxide), thus preparing a collagen gel film (200 to 300 µm thick). 10 mL of a cell suspension of $2.0 \times 10^4$ cells/mL human skin fibroblasts suspended in DMEM medium supplemented with 10.0% fetal bovine serum was prepared, 3.6 mL was seeded on each of the collagen gel films, and culturing was carried out in an incubator with 5% carbon dioxide at 37° C. for 24 hours, thus preparing a cell sheet. The result of examining the state of the cells after 24 hours using an optical microscope was the same as in FIG. 12.

—Chemical Synthesis of Polypeptide Having Peptide Sequence Present in Elastin—

With regard to production of an elastin-derived polypeptide that can be used in a temperature responsive sheet in the same way as for a chemically modified water-soluble elastin, an example of the production (polymerization) of poly (VPGVG) (SEQ ID NO:1), which is one of the polypeptides, is now explained (see FIG. 14).

—Production of Poly(VPGVG) (SEQ ID NO:1) (1) by Active Ester Method—

H-VPGVG-ONp.TFA (0.23 mmol) was dissolved in DMSO (0.5 mL), the pH was adjusted to 9 using NMM, and stirring was carried out for 7 days to thus carry out polymerization. The sample was subjected to dialysis using a dialysis membrane having a molecular weight cut-off of 3,500 and then lyophilized. The yield was 37%, and the average molecular weight was about 17,000. The average molecular weight was determined by a standard method employing electrophoresis from a reference curve based on a molecular weight marker.

—Production of Poly(VPGVG) (SEQ ID NO:1) (2) by Carbodiimide Method in Organic Solvent—

H-VPGVG-OH.TFA (0.37 mmol) was dissolved in DMSO (0.5 mL), HOBt.H$_2$O (0.37 mmol) was added, 10 minutes later a water-soluble carbodiimide (0.74 mmol) was added, the pH was adjusted to 9 using NMM, and stirring was carried out for 7 days to thus carry out polymerization. The sample was subjected to dialysis using a dialysis membrane having a molecular weight cut-off of 3,500 and then lyophilized. The yield was 61%, and the average molecular weight was about 20,000.

—Production of Poly(VPGVG) (SEQ ID NO:1) (3) by Carbodiimide Method in Water Solvent—

H-VPGVG-OH.TFA (0.37 mmol) was dissolved in distilled water (0.5 mL), Sulfo-NHS (0.37 mmol) was added, a water-soluble carbodiimide (0.37 mmol) was then added, the pH was adjusted to 9 using NMM, and stirring was carried out for 7 days to thus carry out polymerization. The sample was subjected to dialysis using a dialysis membrane having a molecular weight cut-off of 3,500 and then lyophilized. The yield was 6.3%, and the average molecular weight was about 22,000.

[Production of Poly(VPGVG) (SEQ ID NO:1) (4) by Bis(4-Nitrophenyl) Carbonate Method]

H-VPGVG-OH.TFA (0.37 mmol) was dissolved in pyridine (0.5 mL), Bis-PNPC (0.11 mmol) was added, the pH was adjusted to 9 using NMM, and stirring was carried out for 7 days to thus carry out polymerization. The sample was subjected to dialysis using a dialysis membrane having a molecular weight cut-off of 3,500 and then lyophilized. The yield was 16%, and the average molecular weight was about 14,000.

—Measurement of Reversible Turbidity Curve of Poly (VPGVG) (SEQ ID NO:1)—

A 30 mg/mL solution of the poly(VPGVG)(1) (SEQ ID NO:1) produced by the active ester method was prepared by dissolving it in a PBS solution (pH 7.4) at 5° C., and turbidity measurement was carried out when the temperature was increased and decreased in a temperature range of 5° C. to 65°

Figure 15:
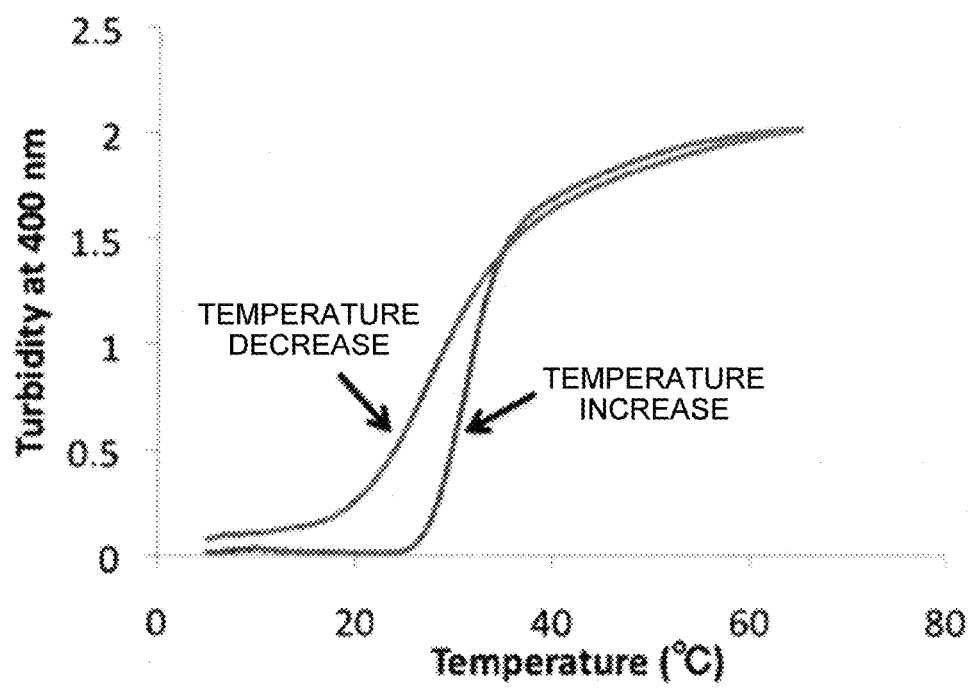
FIG. 15 shows a diagram showing a reversible turbidity curve of the elastin-derived polypeptide poly(VPGVG) (SEQ ID NO: 1).

C. under a flow of nitrogen with a temperature change of 0.5° C./min. The results are shown in FIG. 15. It can be seen from FIG. 15 that with regard to the turbidity curve of poly (VPGVG) (SEQ ID NO:1), the turbidity curve accompanying increase in temperature substantially coincided with the turbidity curve accompanying decrease in temperature and it was reversible. The results of FIG. 15 and FIGS. 1 and 2 indicate that due to coacervation the poly(VPGVG) became cloudy when heated, a coacervate was formed at 37° C. and a pH of 7.4, which were the conditions for cell culturing, and it returned to the original transparent solution state at 20° C. or below.

Figure 16:
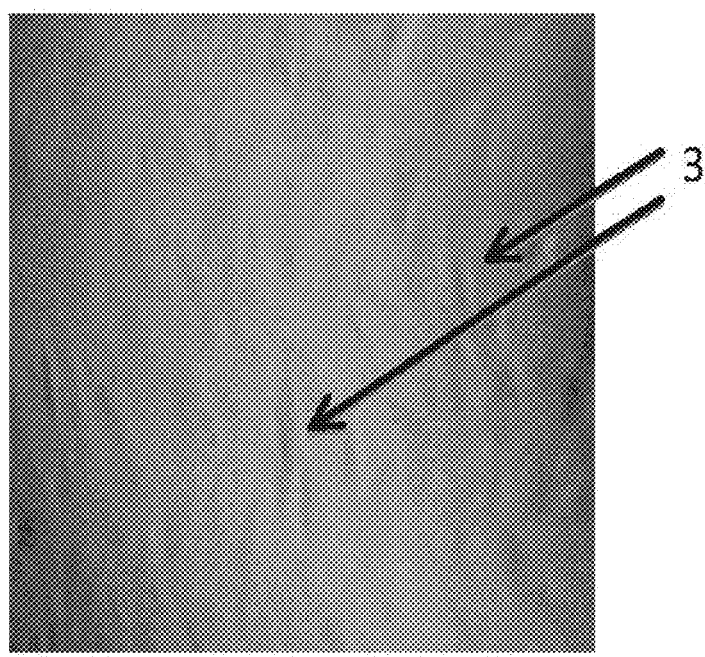
FIG. 16 shows an optical microscope photograph of a fibroblast spindle-shaped state 24 hours after culturing fibroblasts seeded on a collagen gel prepared on a coacervate of the elastin-derived polypeptide poly(VPGVG) (SEQ ID NO:1).

—Preparation of Cell Sheet Using Poly(VPGVG) (SEQ ID NO:1) Coacervate— poly(VPGVG) (1) (SEQ ID NO:1) produced by the active ester method was dissolved in a PBS solution (pH 7.4) to give 30 mg/mL, the solution was sterilized by passing it through a 0.22 μm Filter-Unit sterilization filter, and 100 μL was pipetted into each well of a 96 well culture dish and incubated for 24 hours (60° C., in 5% carbon dioxide), thus separating it into two layers. Subsequently, the upper layer equilibrium solution was removed, and the surface of the lower layer coacervate was dried at 37° C. for about 10 minutes. Subsequently, a 1 mg/mL PBS solution of type I collagen was prepared (sterilized), and 100 μL thereof was added onto each of the coacervates and incubated for 1 hour (37° C., in 5% carbon dioxide), thus preparing a collagen gel film. The collagen gel film of each well was seeded with 100 μL of $2.0 \times 10^4$ cells/mL human skin fibroblasts suspended in DMEM medium supplemented with 10.0% fetal bovine serum, and culturing was carried out in an incubator with 5% carbon dioxide at 37° C. for 24 hours. FIG. 16 is an optical microscope photograph showing that fibroblasts after 24 hours of culturing were present on the collagen gel in a spindle-shaped state, suggesting adhesion, spreading, and proliferation. In FIG. 16, 3 denotes fibroblasts that are adhering, spreading, and proliferating.

—Peeling Off Cell Sheet by Dissolution of Poly(VPGVG) (SEQ ID NO:1) Coacervate—

After a cell sheet was prepared as described above, by cooling to 15° C. and incubating for 30 minutes the poly (VPGVG) (SEQ ID NO:1) coacervate was dissolved, and a cell sheet comprising the fibroblasts and the collagen gel was peeled off. A state in which the adhered, spread, and proliferated cell sheet on the collagen gel had peeled off could be observed by the naked eye. The results were the same as those of FIG. 13. By decreasing the temperature in this way the poly(VPGVG) (SEQ ID NO:1) coacervate was dissolved, and a cell sheet comprising the fibroblasts and the collagen gel was easily produced and recovered without being damaged.

All of the polypeptides can be used as temperature responsive sheets.

INDUSTRIAL APPLICABILITY

Tissue and organs of a living body basically have a structure comprising sheet-shaped cells, with folding into various shapes to form the three-dimensional tissue seen in blood vessels and organs. A technique of preparing such a cell sheet by cell culturing using an extracellular matrix as a scaffold, peeling off from a culture dish, and overlaying it is called cell sheet engineering. However, when preparing a cell sheet, since cells strongly adhere to the culture dish due to an adhesion protein, it is necessary to use a proteolytic enzyme when peeling off, and there is the problem that cells and extracellular matrix are damaged. It has been found that a coacervate of a water-soluble elastin, a chemically modified water-soluble elastin, which is a derivative thereof, or an elastin-derived polypeptide is useful for recovering a cell sheet without damage, and in accordance with the present invention cells can be recovered in sheet form using a biologically derived safe protein and polypeptide, and they can also be utilized in cell sheet engineering.

The invention claimed is:

1. A temperature responsive sheet comprising a chemically modified water-soluble elastin obtained by N-acylating at least some of the primary amines and secondary amines contained in a water-soluble elastin molecule and coupling at least some of the carboxyl groups contained in the molecule with a glycine alkyl ester.

2. The temperature responsive sheet according to claim 1, wherein the N-acetylation is carried out so that the degree of modification as defined by equation (1) is at least 80 mole %, $$\text{Degree of modification (mole \%)} = (1 - B/A) \times 100 \tag{1}$$

wherein A denotes a value obtained by subtracting the average value of the absorbance (wavelength 345 nm) of a blank from the average value of the absorbance of the water-soluble elastin, and B denotes a value obtained by subtracting the average value of the absorbance (wavelength 345 nm) of a blank from the average value of the absorbance of the N-acetylated water-soluble elastin.

3. The temperature responsive sheet according to claim 1, wherein at least 90 mole % of the carboxyl groups are coupled with glycine methyl ester.

4. The temperature responsive sheet according to claim 1, wherein the chemically modified water-soluble elastin has the property of forming a coacervate at a pH of 7.4 and a temperature of 37° C., the coacervate dissolving when the temperature is decreased to 15° C.

5. The temperature responsive sheet according to claim 1, wherein the water-soluble elastin is a high molecular weight water-soluble elastin obtained by removing a low molecular weight fraction by dialysis.

6. The temperature responsive sheet according to claim 1, wherein it is for cell culturing.

7. A process for producing a cell sheet, comprising a step of forming above a support the temperature responsive sheet according to claim 1, a step of preparing above the temperature responsive sheet a gel film comprising exracellular matrices, a step of preparing a cell sheet by culturing cells at 30° C. to 40° C. above the collagen gel layer, and a step of subsequently separating the temperature responsive sheet and the cell sheet at 1° C. to 20° C.

8. The process for producing a cell sheet according to claim 7, wherein the gel film comprising exracellular matrices is selected from the group consisting of: collagen, fibronectin, laminin, polylysine, and gelatin.

9. The process for producing a cell sheet according to claim 7, wherein the gel film is a film of collagen.

* * * * *